United States Patent
Boie et al.

(10) Patent No.: US 6,787,670 B1
(45) Date of Patent: Sep. 7, 2004

(54) GLYOXYL ACID AMIDES, METHOD FOR PRODUCING THEM AND THEIR USE FOR CONTROLLING HARMFUL ORGANISMS

(75) Inventors: Christiane Boie, Leichlingen (DE); Thomas Seitz, Langenfeld (DE); Ulrich Heinemann, Leichlingen (DE); Reiner Fischer, Monheim (DE); Martin Vaupel, Leichlingen (DE); Ulrike Wachendorff-Neumann, Neuwied (DE); Karl-Heinz Kuck, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/130,899

(22) PCT Filed: Nov. 20, 2000

(86) PCT No.: PCT/EP00/11530

§ 371 (c)(1),
(2), (4) Date: May 23, 2002

(87) PCT Pub. No.: WO01/39787

PCT Pub. Date: Jun. 7, 2001

(30) Foreign Application Priority Data

Dec. 2, 1999 (DE) .......................................... 199 58 165

(51) Int. Cl.[7] ..................... C07C 233/09; A61K 31/165
(52) U.S. Cl. ......................... 564/165; 564/164; 514/620
(58) Field of Search ................................ 564/164, 165, 564/134, 138, 142; 514/620

(56) References Cited

U.S. PATENT DOCUMENTS

| 3,932,385 | A | 1/1976 | Cook et al. ............... 260/239.1 |
| 3,966,717 | A | 6/1976 | Cook et al. ............. 260/243 C |
| 3,974,153 | A | 8/1976 | Cook et al. ............. 260/243 C |
| 3,975,376 | A | 8/1976 | Cook et al. ............... 260/239.1 |
| 4,017,515 | A | 4/1977 | Cook et al. ........... 260/332.3 R |
| 4,024,133 | A | 5/1977 | Cook et al. ............. 260/243 C |
| 4,024,137 | A | 5/1977 | Cook et al. ............. 260/243 C |
| 4,033,950 | A | 7/1977 | Cook et al. ............. 260/243 C |
| 4,064,346 | A | 12/1977 | Cook et al. .................... 544/30 |
| 4,079,178 | A | 3/1978 | Cook et al. .................... 544/25 |
| 4,091,209 | A | 5/1978 | Cook et al. .................... 544/16 |
| 4,092,477 | A | 5/1978 | Cook et al. .................... 544/26 |
| 4,093,803 | A | 6/1978 | Cook et al. .................... 544/27 |
| 5,112,860 | A | 5/1992 | Wingert et al. ............. 514/513 |
| 5,187,170 | A | 2/1993 | Wingert et al. ............. 514/351 |
| 5,221,762 | A | 6/1993 | Wingert et al. ............... 560/35 |
| 6,130,251 | A | 10/2000 | Seitz et al. ................. 514/620 |
| 6,441,043 | B1 * | 8/2002 | Seitz et al. ................. 514/599 |

FOREIGN PATENT DOCUMENTS

| WO | 96/23763 | 8/1996 |
| WO | 9803474 | * 1/1998 |
| WO | 98/17630 | 4/1998 |
| WO | 98/58903 | 12/1998 |
| WO | 00/41998 | 7/2000 |

OTHER PUBLICATIONS

J. Heterocycl. Chem., 27(3), Mar.–Apr. 1990, pp. 487–495, Yasuhiro Kamitori, Masaru Hojo, Ryôichi Masuda, Seiji Ohara, Kazuyoshi Kawasaki, Yoshihiko Kawamura and Masakazu Tanaka, "4– and 5–Trifluoromethylimidazoles. Novel Cyclization of Trifluoroacetylated Aldehyde Dimethylhydrazones".

Farmaco Ed. Sci., 35(5), (month unavailable) 1980, pp. 394–404, R. Monguzzi, G. Scarpitta, P. Ventura and G. Pifferi, "Sintesi E Configurazione Di Acidi α–Idrazonofenilacetici".

Justus Liebigs Ann. Chem., 722, (month unavailable) 1969, pp. 29–37, von Hans Neunhoeffer, Margaret Neunhoeffer und Walburg Litizus, "α–Hydrazonocarbonsäureazide, I Aliphatische α–Hydrazonocarbonsäureazide".

Justus Liebigs Ann. Chem., 722, (month unavailable) 1969, pp. 38–44, von Hans Neunhoeffer, "α–Hydrazonocarbonsäureazide, II[1]) Aromatische α–Hydrazonocarbonsäureazide".

Tetrahedron, vol. 27, (month unavailable) 1971, pp. 3431–3436, M.M. Sidky, F.M. Soliman and R. Shabana, The Reaction of Alkyl Phosphites with (N–Phenylbenzimidoyl) Formic Acid.

**Chemical Abstracts, vol. 78, No. 9, Mar. 5, 1973 Columbus, Ohio, US; abstract No. 57925, Leminger, Otakar: "Benzene ring chemistry of alkoxylated beta.–phenethylamines. II..beta.–Phenthylamine sulfates alkoxylated on the ring" XP002178224 abstract & Chem. Prum. (1972), 22(11), 553–7.

* cited by examiner

Primary Examiner—Shailendra Kumar
(74) Attorney, Agent, or Firm—Richard E.L. Henderson; Raymond J. Harmuth

(57) ABSTRACT

The invention relates to novel gloyoxylic acid amides, to a process for their preparation and to their use for controlling harmful organisms.

7 Claims, No Drawings

GLYOXYL ACID AMIDES, METHOD FOR PRODUCING THEM AND THEIR USE FOR CONTROLLING HARMFUL ORGANISMS

This application is a 371 of PCT/FR 00/02122, filed Jul. 21, 2000.

The invention relates to novel glyoxylic acid amides, to a plurality of processes for their preparation and to their use for controlling harmful organisms.

It is already known that certain glyoxylic acid amides with a constitution similar to that of the compounds described below have fungicidal properties (compare, for example WO 96/23763, WO 98/17630 or WO 98/58903). However, in many cases, the fungicidal action of these compounds is unsatisfactory.

This invention provides novel compounds of the general formula (I),

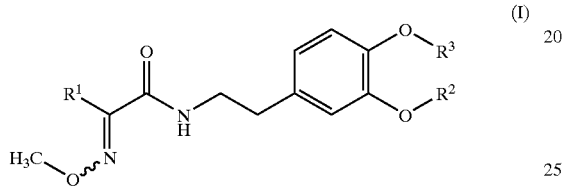

(I)

in which
  $R^1$ represents aryl which optionally has a fused-on cycloalkyl ring, where both the aryl molecule and the cycloalkyl molecule optionally carry further substituents and
  a) $R^2$ represents alkoxyalkyl or optionally methyl- or halogen-substituted arylalkyl, and
    $R^3$ represents optionally substituted alkyl, alkenyl or alkinyl,
  or
  b) $R^2$ represents optionally substituted alkyl, alkoxyalkyl or arylalkyl, and
    $R^3$ represents optionally substituted alkenyl or alkinyl,
  or
  c) $R^2$ represents methyl or ethyl, and
    $R^3$ represents optionally substituted alkyl having at least 3 carbon atoms,
  or
  d) $R^2$ represents alkyl having at least 2 carbon atoms, and
    $R^3$ represents optionally substituted methyl or ethyl.

In the definitions, the saturated or unsaturated hydrocarbon chains, such as alkyl, alkanediyl, alkenyl or alkinyl, are in each case straight-chain or branched, including in combination with heteroatoms, such as in alkoxy, alkylthio or alkylamino.

Halogen generally represents fluorine, chlorine, bromine or iodine, preferably fluorine, chlorine or bromine, in particular fluorine or chlorine.

Aryl represents aromatic mono- or polycyclic hydrocarbon rings, such as, for example, phenyl, naphthyl, anthranyl, phenanthryl, preferably phenyl or naphthyl, in particular phenyl.

Cycloalkyl represents saturated carbocyclic cyclic compounds which optionally form a polycyclic ring system with further carbocyclic fused-on or bridged rings.

Cycloalkenyl represents carbocyclic cyclic compounds which contain at least one double bond and optionally form a polycyclic ring system with further carbocyclic fused-on or bridged rings.

Furthermore, it has been found that the novel glyoxylic acid amides of the general formula (I) have very good action against harmful organisms, in particular a strong fungicidal action.

If appropriate, the compounds according to the invention are present as mixtures of different possible isomeric forms, in particular of stereoisomers, such as for example, E and Z, cis or trans, threo or erythro, and also optical isomers. What is claimed and described are both the E and the Z isomers, and also the threo and erythro and the optical isomers, and any mixtures of these isomers.

The invention preferably provides compounds of the formula (I) in which
  $R^1$ represents aryl which optionally has a fused-on cycloalkyl ring having 3 to 10 ring members, where the cycloalkyl molecule is optionally substituted by 1 to 4 alkyl chains having in each case 1–4 carbon atoms and the aryl molecule is optionally additionally substituted by the substituents listed below:
    Halogen, cyano, nitro, amino, hydroxyl, formyl, carboxyl, carbamoyl, thiocarbamoy);
    in each case straight-chain or branched alkyl, alkoxy, alkylthio, alkylsulfinyl or alkylsulfonyl having in each case 1 to 8 carbon atoms;
    in each case straight-chain or branched alkenyl or alkenyloxy having in each case 2 to 6 carbon atoms;
    in each case straight-chain or branched halogenalkyl, halogenalkoxy, halogenalkylthio, halogenalkylsulfinyl or halogenalkylsulfonyl having in each case 1 to 6 carbon atoms and 1 to 13 identical or different halogen atoms;
    in each case straight-chain or branched halogenylalkenyl or halogenalkenyloxy having in each case 2 to 6 carbon atoms and 1 to 13 identical or different halogen atoms;
    in each case straight-chain or branched alkylamino, dialkylamino, alkylcarbonyl, alkylcarbonyloxy, alkoxycarbonyl, alkylsulfonyloxy, hydroximinoalkyl or alkoximinoalkyl having in each case 1 to 6 carbon atoms in the individual alkyl molecules;
    cycloalkyl having 3 to 6 carbon atoms, and
  a) $R^2$ represents alkoxyalkyl having a total of 2 to 10 carbon atoms or optionally methyl- or halogen-substituted arylalkyl having 1 to 4 carbon atoms in the alkyl molecule and
    $R^3$ represents optionally cyano-, alkoxy- or alkoxycarbonyl-substituted alkyl having 1 to 8 carbon atoms, alkenyl or alkinyl having from 2 to 8 carbon atoms,
  or
  b) $R^2$ represents alkyl having 1 to 8 carbon atoms or optionally methyl- or halogen-substituted arylalkyl having 1 to 4 carbon atoms in the alkyl molecule and
    $R^3$ represents optionally cyano-, alkoxy- or alkoxycarbonyl-substituted alkenyl or alkinyl having 2 to 8 carbon atoms,
  or
  c) $R^2$ represents methyl or ethyl, and
    $R^3$ represents optionally cyano-, alkoxy- or alkoxycarbonyl-substituted alkyl having at least 3 carbon atoms,
  or
  d) $R^2$ represents alkyl having at least 2 carbon atoms, and
    $R^3$ represents optionally cyano-, alkoxy- or alkoxycarbonyl-substituted methyl or ethyl.

The invention relates in particular to compounds of the formula (I) in which $R^1$ represents phenyl which is in each case optionally mono- to trisubstituted and which optionally has fused-on cyclopropyl, cyclobutyl, cyclopentyl, cyclohexyl, cycloheptyl, cylcooctyl or cyclononyl ring, where the cycloalkyl molecule is optionally mono- to tetrasubstituted by methyl, ethyl, n- or i-propyl, n-, i-, s- or t-butyl and the phenyl molecule is optionally additionally substituted by the substituents listed below:

Fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulfinyl or trifluoromethylsulfonyl, methylamino, ethylamino, n- or i-propylamino, dimethylamino, diethylamino, acetyl, propionyl, acetyloxy, methoxycarbonyl, ethoxycarbonyl, methylsulfonyloxy, ethylsulfonyloxy, hydroximinomethyl, hydroximinoethyl, methoximinomethyl, ethoximinomethyl, methoximinoethyl or ethoximinoethyl, cyclopropyl, cyclobutyl, cyclopentyl or cyclohexyl, and a) $R^2$ represents methoxyethyl, ethoxyethyl or optionally methyl-, fluorine- or chlorine-substituted benzyl or phenethyl and
  $R^3$ represents optionally cyano-, methoxy-, ethoxy-, methoxycarbonyl- or ethoxycarbonyl substituted methyl, ethyl, n- or i-propyl, n-, i-, s- or t-butyl, pentyl, hexyl, heptyl, octyl, allyl, methylallyl, crotonyl, propinyl, butinyl or benzyl, or b) $R^2$ represents methyl, ethyl, n- or i-propyl, n-, i-, s- or t-butyl, pentyl, hexyl, heptyl or octyl or optionally methyl-, fluorine- or chlorine-substituted benzyl or phenethyl, and
  $R^3$ represents optionally cyano-, methoxy-, ethoxy-, methoxycarbonyl- or ethoxycarbonyl-substituted allyl, methylallyl, crotonyl, propinyl or butinyl, or c) $R^2$ represents methyl or ethyl, and
  $R^3$ represents optionally cyano-, methoxy-, ethoxy-, methylcarbonyl or ethoxycarbonyl-substituted n- or i-propyl, n-, i-, s- or t-butyl, pentyl, hexyl, heptyl or octyl, or d) $R^2$ represents n- or i-propyl, n-, i-, s- or t-butyl, pentyl, hexyl, heptyl or octyl, and
  $R^3$ represents optionally cyano-, methoxy-, ethoxy-, methoxycarbonyl- or ethoxycarbonyl-substituted methyl or ethyl.

$R^1$ particularly preferably represents para-chlorophenyl, para-bromophenyl, 1,2,3,4-tetrahydronaphthalene or indane.

$R^2$ particularly preferably represents ethyl, in particular methyl.

$R^3$ particularly preferably represents cyanomethyl, allyl or propargyl.

The general or preferred radical definitions given above apply both to the end products of the formula (I) and, correspondingly, to the starting materials or intermediates required in each case for the preparation.

The radical definitions given in the respective combinations or preferred combinations of radicals for these individual radicals are, independently of the combination of radicals given in each case, also replaced by any radical definitions of other preferred ranges.

Finally, it has been found that the novel glyoxylic acid amides of the general formula (I) are obtained when a) Carboxylic acid derivatives of the general formula (II),

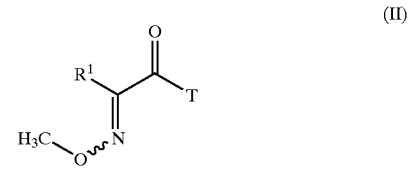

in which
  $R^1$ is as defined above and
  T represents hydroxyl, halogen or alkoxy
are reacted with an amine of the general formula (III)

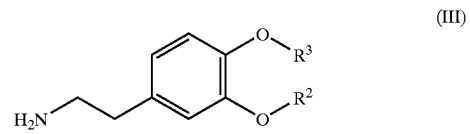

in which
  $R^2$ and $R^3$ are as defined above,
or an acid addition complex thereof
  if appropriate in the presence of an acid acceptor, if appropriate in the presence of a condensing agent and if appropriate in the presence of a diluent.

Finally, it has been found that the novel compounds of the formula (I) have very strong action against harmful organisms.

The formula (II) provides a general definition of the carboxylic acid derivatives required as starting materials for carrying out the process a) according to the invention. In this formula (II), $R^1$ preferably or in particular has those meanings which have already been mentioned in connection with the description of the compounds of the formula (I) according to the invention as being preferred or as being particularly preferred for $R^1$; T preferably represents alkoxy having 1 to 4 carbon atoms, in particular methoxy or ethoxy, represents hydroxyl or chlorine.

The starting materials of the formula (II) are known and/or can be prepared by processes known per se (cf. EP-A 493 711, EP-A 432 503, DE-A 3 938 054, J. Heterocycl. Chem. (1990), 27(3), 487–95, Farmaco, Ed. Sci. (1980), 35(5), 394–404, Justus Liebigs Ann. Chem. (1969), 722, 38–44, Justus Liebigs Ann. Chem. (1969), 722, 29–37, Tetrahedron 1971, 3431–6, DE 222 3375.

The formula (III) provides a general definition of the amines furthermore required as starting materials for carrying out the process a) according to the invention. In this formula (III), $R^2$ and $R^3$ preferably or in particular have those meanings which have already been mentioned in connection with the description of the compounds of the formula (I) according to the invention as being preferred or as being particularly preferred for $R^2$ and $R^3$.

Some of the amines of the formula (III) are known organic chemicals for synthesis, and/or they can be prepared by processes known per se.

Novel and also part of the subject-matter of the present invention are amines of the formula (III-a),

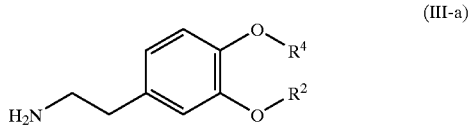
(III-a)

in which
R² is as defined above and
R⁴ represents allyl, propargyl or cyanomethyl.

The amines of the formula (III-a) are obtained (process b) when hydroxy compounds of the general formula (IV),

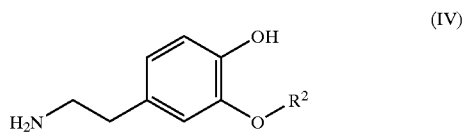
(IV)

in which
R² is as defined above,
are reacted with allyl chloride, allyl bromide, allyl iodide or propargyl chloride, propargyl bromide or propargyl iodide or chloro- bromo- or iodacetonitrile, if appropriate in the presence of a diluent, such as, for example, acetonitrile, and if appropriate in the presence of an acid acceptor, such as, for example, potassium carbonate.

If appropriate, the amino group of the compounds of the formula (IV) is, prior to the reaction, provided by customary methods with a protective group customary for amines, such as, for example, t-butoxycarbonyl. This gives compounds of the formula (IV*),

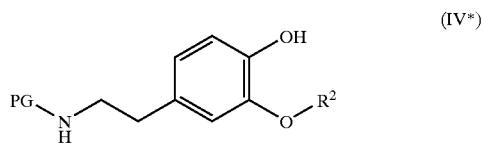
(IV*)

in which
R² is as defined above and
PG represents the protective group
which, after the reaction which initially gives compounds of the formula (II-a*),

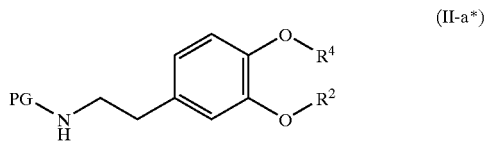
(II-a*)

in which
R², R⁴ and PG are as defined above
is removed using methods known from the literature (see also the Preparation Examples). Depending on the work-up, the free amines or their salts, for example hydrochlorides, are formed.

The formula (IV) provides a general definition of the hydroxyl compounds required as starting materials for carrying out the process b) according to the invention. In this formula (IV), R² preferably or in particular has those meanings which have already been mentioned in connection with the description of the compounds of the formula (I) according to the invention as being preferred or as being particularly preferred for R².

The hydroxyl compounds of the formula (IV) are commercial chemicals for synthesis or can be obtained by known methods (compare, for example J. Chem. Soc. 127 (1925), 560 and J. Amer. Chem. Soc. 72 (1950), 2781).

The compounds allyl chloride, allyl bromide, allyl iodide or propargyl chloride, propargyl bromide or propargyl iodide or chloro- bromo- or iodioacetonitrile are generally customary chemicals for synthesis.

The process a) according to the invention is, if appropriate, carried out in the presence of a diluent. Suitable diluents are water and organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; nitrites, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate.

If appropriate, the process a) according to the invention is carried out in the presence of a suitable acid acceptor. Suitable acid acceptors are all customary inorganic or organic bases. These include, for example, alkaline earth metal or alkali metal hydroxides, alkoxides, acetates, carbonates or bicarbonates, such as, for example, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate, or sodium bicarbonate, and also tertiary amines, such as trimethylamine, triethylamine, tributylamine, N,N-dimethylaniline, N,N-dimethylbenzylamine, pyridine, N-methylpiperidine, N,N-dimethylaminopyridine, diazabicyclooctane (DABCO), diazabicyclononene (DBN) or diazabicycloundecene (DBU).

The process a) according to the invention is, if appropriate, carried out in the presence of a suitable condensing agent. Suitable condensing agents are all condensing agents which are customarily used for such amidation reactions. Acid halide formers, such as phosgene, phosphorus tribromide, phosphorus trichloride, phosphorus pentachloride, phosphorus oxychloride or thionyl chloride; anhydride formers such as ethyl chloroformate, methyl chloroformate, isobutyl chloroformate or methanesulfonyl chloride; carbodiimides, such as N,N'-dicyclohexylcarbodiimide (DCC) or other customary condensing agents, such as phosphorus pentoxide, polyphosphoric acid, N,N'-carbonyldiimidazole, 2-ethoxy-N-ethoxycarbonyl-1,2-dihydroquinoline (EEDQ) or triphenylphosphine/carbon tetrachloride may be mentioned by way of example.

The process a) according to the invention is, if appropriate, carried out in the presence of a catalyst. Examples which may be mentioned are 4-dimethylaminopyridine, 1-hydroxy-benzotriazole or dimethylformamide.

When carrying out the process a) according to the invention, the reaction temperatures can be varied within a relatively wide range. In general, the process is carried out at temperatures between −50° C. and +150° C., preferably at temperatures between −20° C. and 150° C.

For carrying out the process a) according to the invention, in general from 1 to 5 mol, preferably from 1.0 to 2.5 mol, of amine are employed per mole of carboxylic acid derivative of the formula (II).

The practice of the reaction and the work-up and isolation of the reaction products are carried out by known processes (cf. the preparation examples).

The process a) according to the invention can also be carried out as a two-step process. Here, the carboxylic acid derivatives of the general formula (II) are initially converted into an activated form and, in a subsequent step, reacted with the amines of the general formula (III) to give the glyoxalic acid amides of the general formula (I) according to the invention.

Suitable activated forms of the carboxylic acid derivatives of the formula (II) are all carboxyl-activated derivatives, such as, for example, acid halides, preferably acid chlorides, acid azides, furthermore symmetrical and mixed anhydrides, such as, for example, the mixed o-alkylcarbonic anhydrides, additionally activated esters, such as, for example, p-nitrophenyl esters or N-hydroxisuccinimidates, and also adducts with condensing agents, such as, for example, dicyclohexylcarbodiimide or activated forms of the carboxylic acids generated in situ.

The processes according to the invention are generally carried out under atmospheric pressure. However, it is also possible to operate under elevated or reduced pressure—in general between 0.1 bar and 10 bar.

The practice of the reaction and the work-up and isolation of the reaction products is carried out by known processes.

The compounds according to the invention have a strong microbicidal action and can be employed for controlling undesirable harmful organisms, in particular microorganisms, such as fungi and bacteria, in crop protection and in the protection of materials.

Fungicides are employed [lacuna] crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

At certain concentrations, the compounds according to the invention also have herbicidal or insecticidal action.

Some pathogens causing fungal and bacterial diseases which come under the generic names listed above are mentioned as examples, but not by way of limitation:

Xanthomonas species, such as, for example, *Xanthomonas campestris* pv. *oryzae*;

Pseudomonas species, such as, for example, *Pseudomonas syringae* pv. *lachrymans*;

Erwinia species, such as, for example, *Erwinia amylovora*;

Pythium species, such as, for example, *Pythium ultimum*;

Phytophthora species, such as, for example, *Phytophthora infestans*;

Pseudoperonospora species, such as, for example, *Pseudoperonospora humuli* or *Pseudoperonospora cubensis*;

Plasmopara species, such as, for example, *Plasmopara viticola*;

Bremia species, such as, for ex ample, *Bremia lactucae*;

Peronospora species, such as, for example, *Peronospora pisi* or *P. brassicae*;

Erysiphe species, such as, for example, *Erysiphe graminis*;

Sphaerotheca species, such as, for example, *Sphaerotheca fuliginea*;

Podosphaera species, such as, for example, *Podosphaera leucotricha*;

Venturia species, such as, for example, *Venturia inaequalis*;

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus*;

Puccinia species, such as, for example, *Puccinia recondita*;

Sclerotinia species, such as, for example, *Sclerotinia sclerotiorum*;

Tilletia species, such as, for example, *Tilletia caries*;

Ustilago species, such as, for example, *Ustilago nuda* or *Ustilago avenae*;

Pellicularia species, such as, for example, *Pellicularia sasakii*;

Pyricularia species, such as, for example, *Pyricularia oryzae*;

Fusarium species, such as, for example, *Fusarium culmorum*;

Botrytis species, such as, for example, *Botrytis cinerea*;

Septoria species, such as, for example, *Septoria nodorum*;

Leptosphaeria species, such as, for example, *Leptosphaeria nodorum*;

Cercospora species, such as, for example, *Cercospora canescens*;

Alternaria species, such as, for example, *Alternaria brassicae*; and

Pseudocercosporella species, such as, for example, *Pseudocercosporella herpotrichoides*.

The fact that the active compounds are well tolerated by plants at the concentrations required for controlling plant diseases permits the treatment of aerial parts of plants, of propagation stock and seeds, and of the soil.

According to the invention, it is possible to treat all plants and parts of plants. Plants are to be understood here as meaning all plants and plant populations such as desired and undesired wild plants or crop plants (including naturally occurring crop plants).

Crop plants can be plants which can be obtained by conventional breeding and optimization methods or by biotechnological and genetic engineering methods or combinations of these methods, including the transgenic plants and including plant cultivars which can or cannot be protected by varietal protection rights. Parts of plants are to be understood as meaning all above-ground and below-ground parts and organs of plants, such as shoot, leaf, flower and root, examples which may be mentioned being leaves, needles, stems, trunks, flowers, shoot-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compounds according to the invention can be employed particularly successfully for controlling diseases in viticulture, fruit and vegetable growing, such as, for example, against Alternaria, Phytophtora and Plasmopara species.

Furthermore, the active compounds according to the invention may also be employed to increase the yield of crops. Moreover, they have reduced toxicity and are tolerated well by plants.

The compounds according to the invention can be used in connection with all plants and plant cultivars including transgenic plants and plant cultivars, where, in the case of transgenic plants and plant cultivars, synergistic effects may occur.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ for example organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates. Suitable dispersants are: for example lignin-sulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention, as such or in their formulations, can also be used as a mixture with known fungicides, bactericides, acaricides, nematicides or insecticides, for example to widen the activity spectrum or to prevent the build-up of resistance. In many cases, synergistic effects are thereby obtained, i.e. the activity of the mixture is greater than the activity of the individual components.

Examples of co-components are the following compounds:

Fungicides:

aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulfide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamnine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminum, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulfate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), quinomethionate, sulfur and sulfur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, 1-isopropyl{2-methyl-1-[[[1-(4-methylphenyl)ethyl]-amino]carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidindione, 1-[(diiodomethyl)-sulfonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulfonyl]-5-(trichloromethyl)-1,3,4-thiadiazole, 2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulfonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulfate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium bicarbonate, methanetetrathiol-sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulfonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H-1-benzopyrane-2,1'(3'H)-isobenzofuran-3'-one,
Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.
Insecticides/Acaricides/Nematicides:
abamectin, acephate, acelamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypertnethrin, cyromazine,
deltamethrin, demeton M, demeton S, demeton-S-methyl, diafenthiuron, diazinon, dichlorvos, dicofol, diflubenzuron, dimethoate, dimethylvinphos, diofenolan, disulfoton, docusat-sodium, dofenapyn,
eflusilanate, emamectin, empenthrin, endosulfan, Entomopfthora spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, isazofos, isofenphos, isoxathion, ivermectin,
nuclear polyhedrosis viruses,
lambda-cyhalothrin, lufenuron,
malathion, mecarbam, metaldehyde, methamidophos, Metharhizium anisopliae, Metharhizium flavoviride, methidathion, methiocarb, methomyl, methoxyfenozide, metolcarb, metoxadiazone, mevinphos, milbemectin, monocrotophos,
naled, nitenpyram, nithiazine, novaluron,
omethoate, oxamyl, oxydemethon M,
*Paecilomyces fumosoroseus*, parathion A, parathion M, permethrin, phenthoate, phorate, phosalone, phosmet, phosphamidon, phoxim, pirimicarb, pirinphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, tetradifon, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii*,
YI 5302,
zeta-cypermethrin, zolaprofos,
(1R-cis)-[5-(phenylmethyl])-3-furanyl]-methyl-3-[(dihydro-2-oxo-3(2H)-furanylidene)-methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl)]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]benzamide,
3-methylphenyl propylcarbamate,
4-[4-(4-ethoxyphenyl)-4-methylpenty]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N"-nitro-guanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl[2-(dipropylamino)-2-oxoethyl]-ethylphosphoramidothioate.

It is also possible to admix other known active compounds, such as herbicides, fertilizers and growth regulators.

In addition, the compounds of the formula (I) according to the invention also have very good antimycotic activity. They have a very broad antimycotic activity spectrum in particular against dermatophytes and yeasts, molds and diphasic fungi (for example against Candida species such as *Candida albicans, Candida glabrata*) [lacuna] such as *Epidermophyton floccosum*, Aspergillus species such as *Aspergillus niger* and *Aspergillus fumigatus*, Trichophyton species such as *Trichophyton mentagrophytes*, Microsporon species such as Microsporon canis and audouinii. The list of these fungi does by no means limit the mycotic spectrum covered, but is only for illustration.

The active compounds can be used as such, in the form of their formulations or the usable forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

The examples below serve to illustrate the invention. However, the invention is not limited to the examples.

PREPARATION EXAMPLES

Example 1

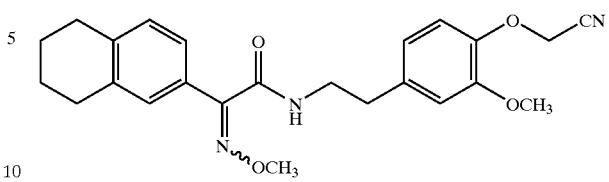

Process a)

2.2 ml (4.4 mmol) of a 2-molar solution of oxalyl chloride in dichloromethane are added to a solution of 0.94 g (4.0 mmol) of 2-(methoxyimino)-2-(5,6,7,8-tetrahydro-2-naphthyl)acetic acid in 15 ml of dichloromethane and 0.5 ml of dimethylformamide, and the mixture is stirred at room temperature for 2 hours. The mixture is concentrated under reduced pressure and dissolved in 15 ml of tetrahydrofuran. This solution is added to a solution, cooled to 0° C., of 1.37 g (4.0 mmol) of 2-[4-(cyanomethoxy)-3-methoxy-phenyl]-1-ethanaminium chloride and 1.2 ml (8.6 mmol) of triethylamine in 30 ml of tetrahydrofuran. The mixture is stirred without further cooling for 18 hours, and the precipitate is filtered off. The filtrate is concentrated, taken up in 200 ml of dichloromethane, washed with water, dried over sodium sulfate and reconcentrated. The residue is chromatographed on silica gel using petroleum ether/ethyl acetate (10:1). This gives 1.3 g (77% of theory) of N-[4-(cyanomethoxy)-3-methoxyphenethyl]-2-(methoxyimino)-2-(5,6,7,8-tetrahydro-2-naphthyl)acetamide as a mixture of isomers.

HPLC:
Isomer A: log P=3.16
Isomer B: log P=3.41

The log P values were determined in accordance with EEC directive 79/831 annex V. A8 by HPLC (gradient method, acetonitrile/0.1% aqueous phosphoric acid)

Analogously to Example 1, and in accordance with the general description of the preparation processes according to the invention, it is also possible to prepare the compounds of the formula (I) listed in Table 1 below:

TABLE 2

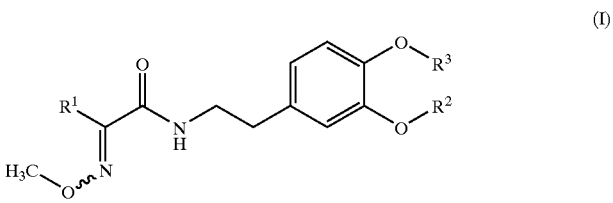

(I)

| Ex. | $R^1$ | $R^2$ | $R^3$ | isomer | logP |
|---|---|---|---|---|---|
| 2 | 4-bromophenyl | —$CH_3$ | n-propyl | E/Z | 3.61/3.88 |
| 3 | 4-bromophenyl | —$CH_3$ | n-propyl | E | 3.61 |
| 4 | 4-bromophenyl | —$CH_3$ | n-propyl | Z | 3.88 |
| 5 | 4-chlorophenyl | —$CH_3$ | n-propyl | E/Z | 3.52/3.78 |
| 6 | 4-chlorophenyl | —$CH_3$ | n-propyl | Z | 3.78 |
| 7 | 4-chlorophenyl | —$CH_3$ | n-propyl | E | 3.52 |
| 8 | 4-ethylphenyl | —$CH_3$ | n-propyl | E/Z | 3.64/3.91 |
| 9 | 4-ethylphenyl | —$CH_3$ | n-propyl | Z | 3.91 |
| 10 | 4-ethylphenyl | —$CH_3$ | n-propyl | E | 3.64 |
| 11 | 4-tolyl | —$CH_3$ | n-propyl | E/Z | 3.30/3.58 |
| 12 | 4-tolyl | —$CH_3$ | n-propyl | Z | 3.58 |
| 13 | 4-tolyl | —$CH_3$ | n-propyl | E | 3.30 |

TABLE 2-continued (I)

| Ex. | R¹ | R² | R³ | isomer | logP |
|---|---|---|---|---|---|
| 14 | 5-methylindanyl | —CH₃ | n-propyl | E/Z | |
| 15 | 5-methylindanyl | —CH₃ | n-propyl | Z | 3.98 |
| 16 | 5-methylindanyl | —CH₃ | n-propyl | E | 3.71 |
| 17 | 6-methyltetrahydronaphthyl | —CH₃ | n-propyl | E/Z | 4.00/4.29 |
| 18 | 6-methyltetrahydronaphthyl | —CH₃ | n-propyl | E | 4.00 |
| 19 | 6-methyltetrahydronaphthyl | —CH₃ | n-propyl | Z | 4.29 |
| 20 | 4-chlorophenyl | —CH₃ | s-butyl | E/Z | 4.06/4.34 |
| 21 | 4-chlorophenyl | —CH₃ | s-butyl | Z | 4.34 |
| 22 | 4-chlorophenyl | —CH₃ | s-butyl | E | 4.06 |
| 23 | 4-bromophenyl | —CH₃ | s-butyl | E/Z | 3.91/4.19 |
| 24 | 4-bromophenyl | —CH₃ | s-butyl | Z | 4.19 |
| 25 | 4-bromophenyl | —CH₃ | s-butyl | E | 3.91 |
| 26 | 4-tolyl | —CH₃ | s-butyl | E/Z | 3.61/3.88 |
| 27 | 4-tolyl | —CH₃ | s-butyl | Z | 3.88 |
| 28 | 4-tolyl | —CH₃ | s-butyl | E | 3.61 |
| 29 | 4-ethylphenyl | —CH₃ | s-butyl | E/Z | 3.94/4.24 |
| 30 | 4-ethylphenyl | —CH₃ | s-butyl | Z | 4.24 |
| 31 | 4-ethylphenyl | —CH₃ | s-butyl | E | 3.94 |
| 32 | 4-chlorophenyl | —CH₃ | n-butyl | E/Z | 3.89/4.16 |
| 33 | 4-chlorophenyl | —CH₃ | n-butyl | Z | 4.16 |
| 34 | 4-chlorophenyl | —CH₃ | n-butyl | E | 3.89 |
| 35 | 4-bromophenyl | —CH₃ | n-butyl | E/Z | 4.01/4.30 |
| 36 | 4-bromophenyl | —CH₃ | n-butyl | Z | 4.30 |
| 37 | 4-bromophenyl | —CH₃ | n-butyl | E | 4.01 |
| 38 | 4-tolyl | —CH₃ | n-butyl | E/Z | 3.74/3.99 |
| 39 | 4-tolyl | —CH₃ | n-butyl | Z | 3.99 |
| 40 | 4-tolyl | —CH₃ | n-butyl | E | 3.74 |
| 41 | 4-ethylphenyl | —CH₃ | n-butyl | E/Z | 4.03/4.34 |
| 42 | 4-ethylphenyl | —CH₃ | n-butyl | Z | 4.34 |
| 43 | 4-ethylphenyl | —CH₃ | n-butyl | E | 4.03 |
| 44 | 6-methyltetrahydronaphthyl | —CH₃ | i-butyl | E/Z | 4.45/4.74 |

TABLE 2-continued

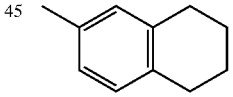
(I)

| Ex. | R¹ | R² | R³ | isomer | logP |
|---|---|---|---|---|---|
| 45 | 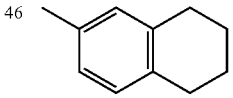 | —CH₃ | i-butyl | Z | 4.74 |
| 46 | 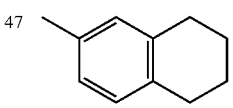 | —CH₃ | i-butyl | E | 4.45 |
| 47 | 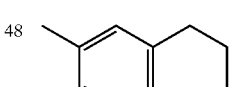 | —CH₃ | n-butyl | E/Z | 4.40/4.68 |
| 48 | 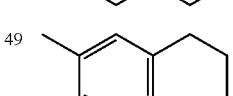 | —CH₃ | n-butyl | Z | 4.68 |
| 49 | 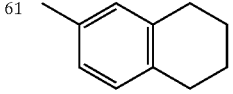 | —CH₃ | n-butyl | E | 4.40 |
| 50 | 4-bromophenyl | —CH₃ | i-propyl | E/Z | 3.51/3.78 |
| 51 | 4-bromophenyl | —CH₃ | i-propyl | E | 3.51 |
| 52 | 4-chlorophenyl | —CH₃ | i-propyl | E/Z | 3.41/3.67 |
| 53 | 4-chlorophenyl | —CH₃ | i-propyl | Z | 3.67 |
| 54 | 4-chlorophenyl | —CH₃ | i-propyl | E | 3.41 |
| 55 | 4-tolyl | —CH₃ | i-propyl | E/Z | 3.20/3.47 |
| 56 | 4-tolyl | —CH₃ | i-propyl | Z | 3.47 |
| 57 | 4-tolyl | —CH₃ | i-propyl | E | 3.20 |
| 58 | 4-ethylphenyl | —CH₃ | i-propyl | E/Z | 3.54/3.83 |
| 59 | 4-ethylphenyl | —CH₃ | i-propyl | Z | 3.83 |
| 60 | 4-ethylphenyl | —CH₃ | i-propyl | E | 3.54 |
| 61 | 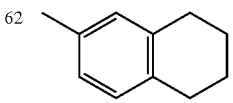 | —CH₃ | i-propyl | E/Z | 3.89/4.18 |
| 62 | 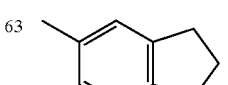 | —CH₃ | i-propyl | E | 3.89 |
| 63 | 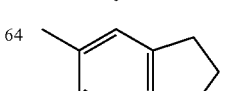 | —CH₃ | i-propyl | E/Z | 3.61/3.87 |
| 64 | 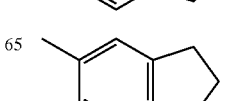 | —CH₃ | i-propyl | Z | 3.87 |
| 65 | | —CH₃ | i-propyl | E | 3.61 |
| 66 | 4-chlorophenyl | —CH₃ | i-butyl | E/Z | 5.32/5.82 |

TABLE 2-continued (I)

| Ex. | R¹ | R² | R³ | isomer | logP |
|---|---|---|---|---|---|
| 67 | 4-chlorophenyl | —CH₃ | i-butyl | Z | 5.82 |
| 68 | 4-chlorophenyl | —CH₃ | i-butyl | E | 5.32 |
| 69 | 4-bromophenyl | —CH₃ | i-butyl | E/Z | 4.06/4.34 |
| 70 | 4-bromophenyl | —CH₃ | i-butyl | Z | 4.34 |
| 71 | 4-bromophenyl | —CH₃ | i-butyl | E | 4.06 |
| 72 | 4-bromophenyl | —CH₃ | n-pentyl | Z | 5.68 |
| 73 | 4-tolyl | —CH₃ | n-pentyl | E/Z | 4.41 |
| 74 | (5-indanyl) | —CH₃ | n-pentyl | E | 4.77 |
| 75 | 4-ethylphenyl | —CH₃ | n-pentyl | E/Z | 4.45/4.74 |
| 76 | 4-ethylphenyl | —CH₃ | n-pentyl | Z | 4.73 |
| 77 | 4-ethylphenyl | —CH₃ | n-pentyl | E | 4.45 |
| 78 | 4-chlorophenyl | benzyl | benzyl | E/Z | 4.95/4.69 |
| 79 | 4-chlorophenyl | benzyl | benzyl | E | 4.69 |
| 80 | 4-tolyl | benzyl | benzyl | E/Z | 4.75/4.50 |
| 81 | 4-chlorophenyl | —CH₃ | n-pentyl | Z | 4.59 |
| 82 | 4-chlorophenyl | —CH₃ | n-pentyl | E/Z | 4.32/4.59 |
| 83 | 4-chlorophenyl | —CH₃ | n-pentyl | E | 4.32 |
| 84 | 4-bromophenyl | benzyl | benzyl | E/Z | 4.77 |
| 85 | 4-bromophenyl | benzyl | benzyl | Z | 5.03 |
| 86 | 4-bromophenyl | benzyl | benzyl | E | 4.75 |
| 87 | 4-ethylphenyl | benzyl | benzyl | Z | 5.06 |
| 88 | (5-indanyl) | benzyl | benzyl | E/Z | 4.66/5.10 |
| 89 | 4-tolyl | —CH₃ | n-heptyl | E/Z | 4.95/5.25 |
| 90 | 4-bromophenyl | —CH₃ | n-heptyl | Z | 5.51 |
| 91 | 4-bromophenyl | —CH₃ | n-heptyl | E/Z | 5.24/5.51 |
| 92 | 4-bromophenyl | —CH₃ | n-heptyl | E | 5.24 |
| 93 | (6-tetrahydronaphthyl) | benzyl | benzyl | Z | 5.36 |
| 94 | (6-tetrahydronaphthyl) | benzyl | benzyl | E/Z | 5.11/5.35 |
| 95 | (6-tetrahydronaphthyl) | benzyl | benzyl | E | 5.11 |
| 96 | 4-bromophenyl | —C₂H₅ | —CH₃ | Z | 3.39 |
| 97 | 4-bromophenyl | —C₂H₅ | —CH₃ | E | 3.12 |
| 98 | 4-bromophenyl | —C₂H₅ | —CH₃ | E/Z | 3.39/3.12 |
| 99 | (6-tetrahydronaphthyl) | —C₂H₅ | —CH₃ | Z | 3.78 |

TABLE 2-continued

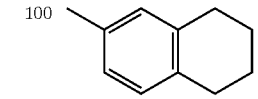

(I)

| Ex. | R¹ | R² | R³ | isomer | logP |
|---|---|---|---|---|---|
| 100 | 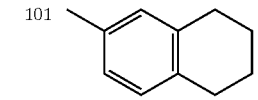 | —C₂H₅ | —CH₃ | E/Z | 3.49 |
| 101 | 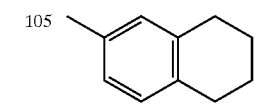 | —C₂H₅ | —CH₃ | Z | 3.49 |
| 102 | 4-chlorophenyl | -i-propyl | -i-propyl | Z | 4.45 |
| 103 | 4-chlorophenyl | -i-propyl | -i-propyl | E/Z | 4.19/4.45 |
| 104 | 4-chlorophenyl | -i-propyl | -i-propyl | E | 4.19 |
| 105 | 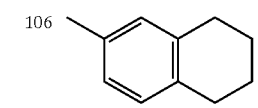 | —CH₃ | 2-methoxyethyl | Z | 3.52 |
| 106 | 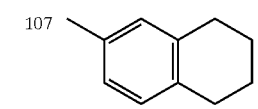 | —CH₃ | 2-methoxyethyl | E/Z | 3.25/3.52 |
| 107 | 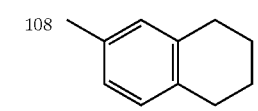 | —CH₃ | 2-methoxyethyl | E | 3.25 |
| 108 | 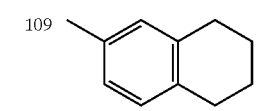 | -i-propyl | -i-propyl | E | 4.70 |
| 109 | 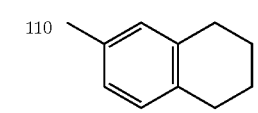 | -i-propyl | -i-propyl | E/Z | 4.70/4.98 |
| 110 | 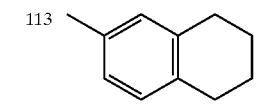 | -i-propyl | -i-propyl | Z | 4.98 |
| 111 | 4-chlorophenyl | —CH₃ | 2-methoxyethyl | Z/E | 3.02/2.77 |
| 112 | 4-tolyl | —CH₃ | 2-methoxyethyl | E/Z | 2.80 |
| 113 | 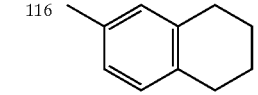 | —CH₃ | —CH₂—COOCH₃ | E/Z | 3.16/3.41 |
| 114 | 4-bromophenyl | —CH₃ | —CH₂—COOCH₃ | E/Z | 2.80/3.06 |
| 115 | 4-bromophenyl | —CH₃ | allyl | E/Z | 3.33/3.60 |
| 116 | 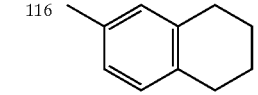 | —CH₃ | allyl | E/Z | 3.71 |

TABLE 2-continued

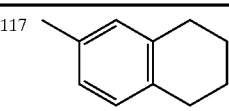

(I)

| Ex. | R¹ | R² | R³ | isomer | logP |
|---|---|---|---|---|---|
| 117 | 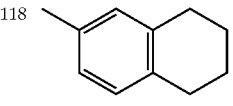 | —CH₃ | —CH₂—C≡CH | E/Z | 3.36/3.64 |
| 118 | 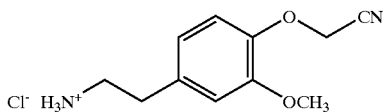 | —CH₃ | —CH₂—C≡C—CH₃ | E/Z | 3.69/3.95 |

The log P values were determined in accordance with EEC directive 79/831 annex V. A8 by HPLC (gradient method, acetonitrile/0.1% aqueous phosphoric acid)

Preparation of the Amines of the Formula (II-a):

Example (II-a-1)

Cl⁻ H₃N⁺—CH₂CH₂—C₆H₃(OCH₃)—O—CH₂CN

Process b (using a protective group)

7.0 g (32 mmol) of di-tert-butyl pyrocarbonate are added to a solution of 6.2 g (30.4 mmol) of 4-hydroxy-3-methoxyphenethylamine hydrochloride in 50 ml of ethyl acetate and 5 ml of triethylamine, and the mixture is stirred at room temperature for 18 hours. 100 ml of ethyl acetate are then added, and the mixture is washed with 50 ml of water, then with 50 ml of dilute citric acid and 50 ml of sodium bicarbonate solution and finally with 50 ml of saturated sodium chloride solution. The organic phase is dried over sodium sulfate and concentrated under reduced pressure.

This gives 7.8 g (96% of theory) of tert-butyl 4-hydroxy-3-methoxyphenethylcarbamate (compound IV*–1)

HPLC: log P=2,09

1.7 g (22.5 mmol) of chloroacetonitrile, 3 g of anhydrous potassium carbonate and 0.1 g of potassium iodide are added to a solution of 2,4 g (9.0 mmol) of tert-butyl 4-hydroxy-3-methoxyphenethylcarbamate (compound IV*–1) in 20 ml of acetonitrile, and the mixture is heated under reflux for 18 hours. The reaction mixture is poured into 100 ml of water and extracted with 200 ml of ether. The organic phase is washed twice with 10% strength aqueous sodium hydroxide solution, dried over sodium sulfate and concentrated. This gives 2.0 g (73% of theory) of tert-butyl 4-(cyanomethoxy)-3-methoxyphenethylcarbamate (compound II-a*–1).

(HPLC: log P=2.51).

3 ml of a saturated ethyl hydrogen chloride solution, added to a solution of 2.0 g (6.5 mmol) of tert-butyl 4-(cyanomethoxy)-3-methoxyphenethylcarbamate (compound II-a*–1) in 10 ml of ethyl acetate, the mixture is stirred for 18 hours and the resulting precipitate is filtered off. The latter is washed twice with ethyl acetate and dried under reduced pressure. This gives 1.6 g (73% of theory) of 2-[4-(cyanomethoxy)-3-methoxyphenyl]-1-ethanaminium chloride.

(HPLC: log P=0.10).

Analogously to Example (II-a-1), and in accordance with the general description of the preparation processes according to the invention, it is also possible to prepare the compounds of the formula (I) listed in Table 2 below:

TABLE 2

(II-a)

H₂N—CH₂CH₂—C₆H₃(O—R⁴)(O—R²)

| Ex. | R² | R⁴ | Salt | logP | m. p. (° C.) |
|---|---|---|---|---|---|
| II-a-2 | —CH₃ | n-propyl | | 0.9 | |
| II-a-3 | —CH₃ | -i-propyl | | 0.83 | |
| II-a-4 | —CH₃ | i-butyl | | | |
| II-a-5 | —CH₃ | 2-butyl | | | |
| II-a-6 | —CH₃ | n-butyl | | | |
| II-a-7 | —CH₃ | 2-methoxyethyl | | 0.32 | |
| II-a-8 | —CH₃ | n-heptyl | hydrochloride | 2.06 | |
| II-a-9 | —CH₃ | 2-methoxyethyl | hydrochloride | 0.36 | |
| II-a-10 | -i-propyl | -i-propyl | hydrochloride | 1.36 | |
| II-a-11 | -i-propyl | —CH₃ | | 0.79 | |
| II-a-11 | —CH₃ | benzyl | | 1.42 | 85–90 |
| II-a-12 | —CH₃ | n-pentyl | | 1.49 | |
| II-a-13 | benzyl | benzyl | hydrochloride | 1.79 | |
| II-a-14 | —CH₃ | allyl | | 0.75 | |
| II-a-15 | —CH₃ | propargyl | | 0.51 | |

The log P values were determined in accordance with EEC directive 79/831 annex V. A8 by HPLC (gradient method, acetonitrile/0.1% aqueous phosphoric acid).

USE EXAMPLES

Example A
Phytophthora Test (Tomato)/Protective

Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Phytophthora infestans. The plants are then placed in an incubation cabin at about 20° C. and 100% relative atmospheric humidity.

Evaluation is carried out 3 days after the inoculation. 0% means an efficacy which corresponds to that of the control, whereas an efficacy of 100% means that no infection was observed.

In this test, the compounds according to the invention listed in Examples (3, 52, 57, 60, 61, 62, 63, 65, 107, 113, 115, 116) exhibit an efficacy of 89% or more at an application rate of 50 g/ha.

TABLE A

Phylophthora test (tomato)/protective

| Active Compound | application rate of active compound in g/ha | efficacy in % |
|---|---|---|
| (107) | 50 | 92 |
| (115) | 50 | 100 |
| (116) | 50 | 99 |
| (113) | 50 | 89 |

TABLE A-continued

Phylophthora test (tomato)/protective

| Active Compound | application rate of active compound in g/ha | efficacy in % |
|---|---|---|
| (3) | 50 | 94 |
| (52) | 50 | 89 |
| (61) | 50 | 94 |
| (63) | 50 | 94 |

TABLE A-continued

Phylophthora test (tomato)/protective

| Active Compound | application rate of active compound in g/ha | efficacy in % |
|---|---|---|
| (57) | 50 | 95 |
| (60) | 50 | 94 |
| (65) | 50 | 94 |
| (62) | 50 | 94 |

Example B
Plasmopara Test (Grapevine)/Protective

Solvent: 47 parts by weight of acetone

Emulsifier: 3 parts by weight of alkylaryl polyglycol ether

To produce a suitable preparation of active compound, one part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at about 20° C. and 100% relative atmospheric humidity for 1 day. The plants are then placed in the greenhouse at about 21° C. at about 90% relative atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection was observed.

In this test, the compounds according to the invention listed in Examples (52, 60, 63, 65, 100, 111, 113, 115, 116) exhibit an efficacy of 83% or more at an application rate of 50 g/ha.

TABLE B

Plasmopara test (grapevine)/protective

| Active Compound | application rate of active compound in g/ha | efficacy in % |
| --- | --- | --- |
| (100) | 50 | 93 |
| (111) | 50 | 96 |
| (115) | 50 | 99 |
| (116) | 50 | 93 |

TABLE B-continued
Plasmopara test (grapevine)/protective
| Active Compound | application rate of active compound in g/ha | efficacy in % |
|---|---|---|
|  (113) | 50 | 94 |
| 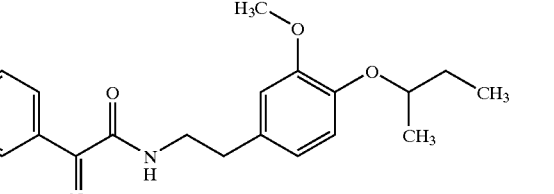 (52) | 50 | 83 |
| 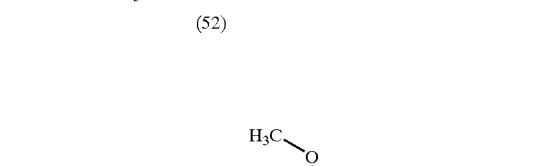 (63) | 50 | 94 |
| 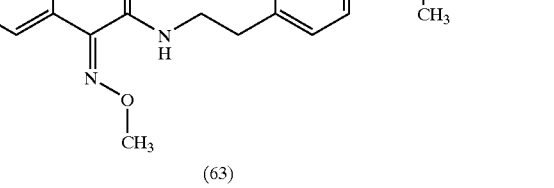 (60) | 50 | 87 |

TABLE B-continued

Plasmopara test (grapevine)/protective

| Active Compound | application rate of active compound in g/ha | efficacy in % |
|---|---|---|
| 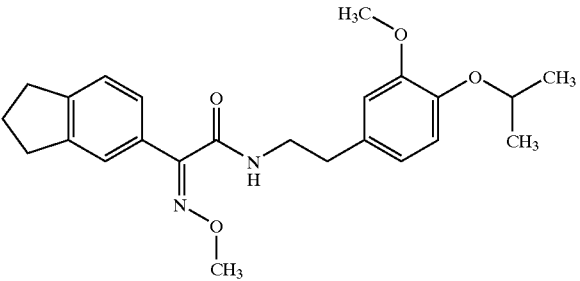 (65) | 50 | 100 |

Example C
Alternaria Test (Tomato)/Protective

Solvent: 50 parts by weight of N,N-dimethylformamide
Emulsifier: 1.2 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration To test for protective activity, young tomato plants are sprayed with the preparation of active compound at the stated application rate. One day after the treatment, the plants are inoculated with a spore suspension of Alternaria solani. The plants then stand at 100% rel. atmospheric humidity and a temperature of 20° C.

Evaluation is carried out 3 days after the inoculation. 0% means an efficacy which corresponds to that of the control, whereas an efficacy of 100% means that no infection is observed.

In this test, the substances according to the invention listed in Examples (45, 46, 48, 49) exhibit an efficacy of 90% or more at an application rate of 750 g/ha.

TABLE C

Alternaria test (tomato)/protective

| Active Compound | application rate of active compound in g/ha | efficacy in % |
|---|---|---|
| 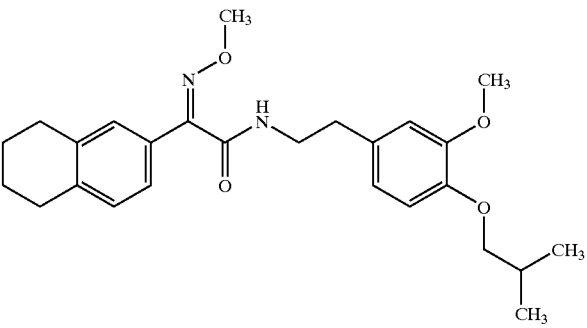 (45) | 750 | 95 |

TABLE C-continued

Alternaria test (tomato)/protective

| Active Compound | application rate of active compound in g/ha | efficacy in % |
|---|---|---|
| (48) | 750 | 95 |
| (49) | 750 | 95 |
| (46) | 750 | 90 |

What is claimed is:

1. A compound of the Formula (I)

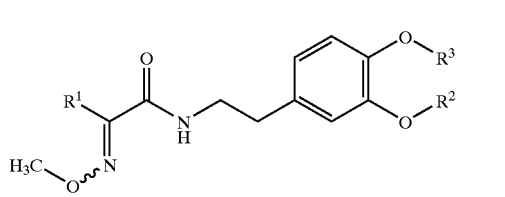

wherein
R¹ represents aryl which optionally has a fused-on cycloalkyl ring, where both the aryl molecule and the cycloalkyl molecule optionally carry further substituents
and
a) R² represents alkoxyalkyl or optionally methyl- or halogen-substituted arylalkyl, and
R³ represents optionally substituted alkyl, alkenyl or alkinyl,
or
b) R² represents optionally substituted alkyl, alkoxyalkyl or arylalkyl, and
R³ represents optionally substituted alkenyl,
or
c) R² represents methyl or ethyl, and
R³ represents optionally substituted alkyl having at least 3 carbon atoms,
or
d) R² represents alkyl having at least 2 carbon atoms, and
R³ represents optionally substituted methyl or ethyl.

2. A compound of the Formula (I) as claimed in claim 1, wherein
R¹ represents aryl which optionally has a fused-on cycloalkyl ring having 3 to 10 ring members, where the cycloalkyl molecule is optionally substituted by 1 to 4 alkyl chains having in each case 1–4 carbon atoms and the aryl molecule is optionally additionally substituted by one or more substituents selected from the group consisting of:
halogen, cyano, nitro, amino, hydroxyl, formyl, carboxyl, carbamoyl, thiocarbamoyl;
straight-chain or branched alkyl, alkoxy, alkylthio, alkylsulfinyl or alkylsulfonyl having in each case 1 to 8 carbon atoms;
straight-chain or branched alkenyl or alkenyloxy having in each case 2 to 6 carbon atoms;
straight-chain or branched halogenalkyl, halogenalkoxy, halogenalkylthio, halogenalkylsulfinyl or halogenalkylsulfonyl having in each case 1 to 6 carbon atoms and 1 to 13 identical or different halogen atoms;
straight-chain or branched halogenalkenyl or halogenalkenyloxy having in each case 2 to 6 carbon atoms and 1 to 13 identical or different halogen atoms;
straight-chain or branched alkylamino, dialkylamino, alkylcarbonyl, alkylcarbonyloxy, alkoxycarbonyl, alkylsulfonyloxy, hydroximinoalkyl or alkoximinoalkyl having in each case 1 to 6 carbon atoms in the individual alkyl molecules; and
cycloalkyl having 3 to 6 carbon atoms, and
wherein
a) R² represents alkoxyalkyl having a total of 2 to 10 carbon atoms or optionally methyl- or halogen-substituted arylalkyl having 1 to 4 carbon atoms in the alkyl molecule and R³ represents optionally cyano-, alkoxy- or alkoxycarbonyl-substituted alkyl having 1 to 8 carbon atoms, alkenyl or alkinyl,
or
b) R² represents alkyl having 1 to 8 carbon atoms or optionally methyl- or halogen-substituted arylalkyl having 1 to 4 carbon atoms in the alkyl molecule and
R³ represents optionally cyano-, alkoxy- or alkoxycarbonyl-substituted alkenyl having 2 to 8 carbon atoms,
or
c) R² represents methyl or ethyl, and
R³ represents optionally cyano-, alkoxy- or alkoxycarbonyl-substituted alkyl having at least 3 carbon atoms,
or
d) R² represents alkyl having at least 2 carbon atoms, and
R³ represents optionally cyano-, alkoxy- or alkoxycarbonyl-substituted methyl or ethyl.

3. A compound of the Formula (I) as claimed in claim 1, wherein
R¹ represents phenyl which is in each case optionally mono- to trisubstituted and which optionally has a fused-on cyclopropyl, cyclobutyl, cyclopentyl, cyclohexyl, cycloheptyl, cylcooctyl or cyclononyl ring, where the cycloalkyl molecule is optionally mono- to tetrasubstituted by methyl, ethyl, n- or i-propyl, n-, i-, s- or t-butyl and the phenyl molecule is optionally additionally substituted by one or more substituents selected from the group consisting of: fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, n-pentyl, n-hexyl, nheptyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, trifluoroethyl, difluoromethoxy, trifluoromethoxy, difluorochloromethoxy, trifluoroethoxy, difluoromethythio, difluorochloromethylthio, trffluoromethylthio, trifuoromethylsulfinyl or trifluoromethylsulfonyl, methylamino, ethylamino, n- or i-propylamino, dimethylamino, diethylamino, acetyl, propionyl, acetyloxy, methoxycarbonyl, ethoxycarbonyl, methylsulfonyloxy, ethylsulfonyloxy, hydroximinomethyl, hydroximinoethyl, methoximinomethyl, ethoximinomethyl, methoximinoethyl or ethoximinoethyl, cyclopropyl, cyclobutyl, cyclopentyl and cyclohexyl,
and
a) R² represents methoxyethyl, ethoxyethyl or optionally methyl-, fluorine- or chlorine-substituted benzyl or phenethyl and
R³ represents optionally cyano, methoxy-, ethoxy-, methoxycarbonyl- or ethoxycarbonyl substituted methyl, ethyl, n- or i-propyl, n-, i-, s- or t-butyl, pentyl, hexyl, heptyl, octyl, allyl, methylallyl, crotonyl, propinyl, butinyl or benzyl,
or
b) R² represents methyl, ethyl, n- or i-propyl, n-, i-, s- or t-butyl, pentyl, hexyl, heptyl or octyl or optionally methyl-, fluorine- or chlorine-substituted benzyl or phenethyl, and
R³ represents optionally cyano-, methoxy-, ethoxy-, methoxycarbonyl- or ethoxycarbonyl-substituted allyl, methylallyl, crotonyl, or c) R² represents methyl or ethyl, and
R³ represents optionally cyano-, methoxy-, ethoxy-, methylcarbonyl or ethoxycarbonyl-substituted n- or i-propyl, n-, i-, s- or t-butyl, pentyl, hexyl, heptyl or octyl, or d) R² represents n- or i-propyl, n-, i-, s- or t-butyl, pentyl, hexyl, heptyl or octyl, and
R³ represents optionally cyano-, methoxy-, ethoxy-, methoxycarbonyl- or ethoxycarbonyl-substituted methyl or ethyl.

4. A compound of the Formula (III-a),

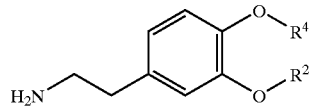

(III-a)

wherein
R² is as defined in claim 1 and
R⁴ represents propargyl or cyanomethyl.

5. A composition for controlling harmful organisms, comprising one or more compounds of the Formula (I) according to claim 1 and one or more extenders and/or carriers and optionally, one or more surfactants.

6. A method for controlling a microorganism selected from the group consisting of fungi, bacteria and combination thereof comprising the step of allowing one or more compounds of the Formula (I) as defined in claim 1 to act on a member selected from the group consisting of said harmful organisms, a habitat of said harmful organisms, and combinations thereof.

7. A process for preparing a composition as defined in claim 5, comprising the step of mixing one or more compounds of the Formula (I) as defined in claim 1 with one or more extenders and/or carriers and/or surfactants.

* * * * *